United States Patent [19]
Geho et al.

[11] Patent Number: 6,063,400
[45] Date of Patent: May 16, 2000

[54] TARGETED LIPOSOMAL CONSTRUCTS FOR DIAGNOSTIC AND THERAPEUTIC USES

[75] Inventors: W. Blair Geho, Wooster; John R. Lau, Howard, both of Ohio

[73] Assignee: SDG, Inc., Cleveland, Ohio

[21] Appl. No.: 09/109,473

[22] Filed: Jul. 2, 1998

Related U.S. Application Data

[60] Provisional application No. 60/052,740, Jul. 2, 1997.

[51] Int. Cl.[7] ..................................................... A61K 9/127
[52] U.S. Cl. ..................... 424/450; 424/1.21; 424/9.321; 424/9.51; 424/417; 424/94.3; 436/829; 935/54; 514/45; 514/49; 514/561; 514/649; 514/663
[58] Field of Search .................................... 424/450, 1.21, 424/9.321, 9.51, 417, 94.3; 436/829; 935/54

[56] References Cited

U.S. PATENT DOCUMENTS

| | | | |
|---|---|---|---|
| 4,659,655 | 4/1987 | Rose | 435/7 |
| 5,049,372 | 9/1991 | Rapaport | 424/1.1 |
| 5,626,870 | 5/1997 | Monshipouri | 424/450 |
| 5,629,215 | 5/1997 | Ribier | 424/450 |

FOREIGN PATENT DOCUMENTS 8800474  1/1988  WIPO .

*Primary Examiner*—Gollamudi S. Kishore
*Attorney, Agent, or Firm*—Frommer Lawerence & Haug LLP

[57] ABSTRACT

This invention provides a liposomal construct for delivering a diagnostic or therapeutic agent to a mammal comprising a liposomal carrier, a diagnostic or therapeutic agent entrapped within or associated with said liposomal carrier and a sequestering agent distributed within said liposomal carrier to reduce leakage of the diagnostic or therapeutic agent from the liposomal construct prior to delivery.

36 Claims, No Drawings

TARGETED LIPOSOMAL CONSTRUCTS FOR DIAGNOSTIC AND THERAPEUTIC USES

This application claims priority from U.S. provisional application Ser. No. 60/052,740, filed Jul. 2, 1997, under 35 USC 119(e)(1).

FIELD OF THE INVENTION

This invention relates generally to liposomal constructs useful for the delivery of biologically active diagnostic and therapeutic agents. In particular, it relates to a high integrity liposomal construct containing a biogenic amine, pharmaceutical compositions thereof, and methods for treating disease states therewith.

DESCRIPTION OF RELATED ART

Various lipid formulations and methods for their preparation have been described for the delivery of pharmaceutically active agents to a host.

Geho and Lau in U.S. Pat. No. 4,603,044 describe a targeted liposomal delivery system for delivery of a drug to the hepatobiliary receptors of the liver. The system is composed of a drug or diagnostic agent encapsulated in or associated with lipid membrane structures in the form of vesicles or liposomes, and a molecule having a fatty substituent attached to the vesicle wall and a target substituent which is a biliary attracted chemical, such as a substituted iminodiacetate complex. The system is particularly useful for the delivery of insulin and serotonin in the treatment of Types I and II diabetes, respectively.

Geho in U.S. Pat. No. 4,761,287 describes the delivery of serotonin to the liver using a hepatocyte directed vesicle (HDV). It was not only shown that the HDV-serotonin construct could deliver effective amounts of serotonin to the hepatocytes, but also that potency was substantially higher than expected.

Geho and Lau in U.S. Pat. No. 4,863,896 disclose that the delivery of insulin in an hepatocyte directed vesicle together with a simultaneous supply of free insulin permits a highly significant reduction in the total daily dosage of insulin required to control blood glucose.

The disclosures of the foregoing patents, as well as that of all other patents and publications referred to in this specification, are explicitly incorporated by reference herein.

SUMMARY OF THE INVENTION

It is an object of this invention to provide means for improving the storage stability and delivery efficiency of diagnostic and therapeutic agents, such as biogenic amines, in liposomal formats.

This invention thus provides a liposomal construct for delivering a diagnostic or therapeutic agent to a mammal comprising a liposomal carrier, a diagnostic or therapeutic agent entrapped within or associated with said liposomal carrier, and a sequestering agent distributed within said liposomal carrier in an amount effective to minimize leakage of the diagnostic or therapeutic agent from the liposomal construct prior to delivery. Preferably, the liposomal construct has targeting moieties associated with its surface for directing the construct to a desired situs.

Also provided are pharmaceutical compositions of the liposomal constructs with pharmaceutically acceptable excipients and methods of treating mammalian conditions with the compositions. Treatment of conditions responsive to biogenic amines, particularly the treatment of Type II diabetes with serotonin or a serotonergic agonist, is especially preferred.

DETAILED DESCRIPTION OF THE INVENTION

In its broadest aspect, this invention provides a liposomal construct for delivering a diagnostic or therapeutic agent to a mammal comprising a liposomal carrier, a diagnostic or therapeutic agent entrapped within or associated with said liposomal carrier, and a sequestering agent distributed within said liposomal carrier in an amount effective to minimize leakage of the diagnostic or therapeutic agent from the liposomal construct prior to delivery.

The particular diagnostic or therapeutic agent employed does not impose any significant limitation upon the scope of the invention. Any agent which is susceptible to liposomal entrapment or association, and the delivery of which may benefit from such association, is expected to be useful, e.g. antibiotics, antidepressants, antitumorigenics, antivirals, cytokines, hormones, imaging agents, neurotransmitters, stimulants, and the like.

In one embodiment, the diagnostic or therapeutic agent is a biogenic amine, including the sympathomimetic amines, naturally occurring catecholamines and mimetics, and autacoids. Representative biogenic amines include, but are not limited to, L-$\beta$-3,4-dihydroxyphenylalanine (L-DOPA), 3-(2-aminoethyl)-5-hydroxyindole (5-hydroxytryptamine or serotonin), 2-(4-imidazolyl)ethylamine (histamine), 4-[1-hydroxy-2-(methylaniuno)ethyl]-1,2-benzenediol (epinephrine), 1-[3,4-dihydroxyphenyl]-2-aminoethanol (norepinephrine), $\gamma$-amino-n-butyric acid, acetylcholine, serotonergic agonists and an amino acid. In preferred embodiment, the biogenic amine is serotonin or a serotonergic agonist. As used herein, the terms "serotonin analog" and "serotonergic agonist" refer to compounds which mimic the activity of serotonin, in particular compounds which act at 5-HT$_{2A/2C}$ receptors of hepatocytes, which interaction is blocked by methysergide.

This invention is based on the discovery that the leakage of biogenic amines from a liposomal construct during storage or following in vivo administration to a warm-blooded host can be minimized by loading the liposomal core volume with nucleotide derivatives, phosphate and phosphatidyl phosphate derivatives, or amino acid polymeric constructs, which trap and sequester the biogenic neurotransmitters within the targeted liposomal delivery system until delivered to the desired site. Leakage need not be eliminated to obtain the object of this invention, but simply reduced to a tolerable amount which will vary with the type of active agent, its initial concentration, end use conditions, and storage variables. Following administration to the host, leakage is considered to be undesirable when an amount of the entrapped agent sufficent to induce a physiological response escapes from the construct prior to arrival at the desired situs.

The liposomal construct contains a sequestering agent selected from nucleotide derivatives, polyphosphate derivatives, phosphatidyl phosphate derivatives, and amino acid polymers. Generically, the sequestering agent comprises a non-diffusible anionic polymer. Nucleotide derivatives include, but are not limited to, adenosine 5'-triphosphate (ATP), cytidine 5'-triphosphate (CTP), guanosine 5'-triphosphate (GTP), thymidine 5'-triphosphate (TTP), uridine 5'-triphosphate (UTP), adenosine 5'-diphosphate (ADP), cytidine 5'-diphosphate (CDP), guanosine 5'-diphosphate (GDP), thymidine 5'-diphosphate (TDP), uridine 5'-diphosphate (UDP), adenosine 5'-monophosphate (AMP), cytidine 5'-monophosphate (CMP), guanosine 5'-monophosphate (GMP), thymidine 5'-monophosphate (TMP), uridine 5'-monophosphate (UMP), adenosine 5'-tetraphosphate, guanosine 5'-tetraphosphate and thymidine 5'-tetraphosphate. The amino acid polymer may be, for example, a copolymer of aspartic acid and glutarnic acid. Polyphosphate derivatives include, but are not limited to, phytic acid and the hexaphosphate of inositol and phosvitin.

In one embodiment, one component of the liposomal carrier membrane is a phosphatidyl phosphate derivative, such as phosphatidic acid, phosphatidyl diphosphate, phosphatidyl triphosphate and phosphatidylinositol-4,5-diphosphate.

Optionally, the liposomal construct has a targeting moiety associated with its surface to bind to a receptor associated with a targeted situs, such as a biliary-attracted molecule. The biliary-attracted molecules may be substituted iminodiacetic acids, N'-substituted derivatives of ethylene diamine-N,N-diacetic acid (EDDA), hepatobiliary dyes, hepatobiliary contrast agents, bile salts, hepatobiliary thiol complexes, and hepatobiliary complexes (including hepatobiliary amine complexes). Specific examples include, but are not limited to, N-(2,6-diisopropylphenylcarbamoylmethyl) iminodiacetic acid, N-(2,6-diethylphenyl carbamoylmethyl) iminodiacetic acid, N-(2,6-dimethylphenylcarbamoylmethyl) iminodiacetic acid, N-(4-isopropylphenylcarbamoylmethyl)iminodiacetic acid, N-(4-butylphenylcarbamoylmethyl)iminodiacetic acid, N-(2,3-dimethylphenylcarbamoyl methyl)iminodiacetic acid, N-(3-butylphenylcarbamoylmethyl)iminodiacetic acid, N-(2-butylphenylcarbamoylmethyl)iminodiacetic acid, N-(4-tertiary-butylphenyl carbamoylmethyl)iminodiacetic acid, N-(3-butoxyphenylcarbamoylmethyl) iminodiacetic acid, N-(2-hexyloxyphenylcarbamoylmethyl)iminodiacetic acid, N-(4-hexyloxyphenylcarbamoylmethyl)iminodiacetic acid; azo substituted iminodiacetic acid, iminodicarboxymethyl-2-naphthyl ketone, phthalein complexone, N-(5, pregnene-3-β-ol-2-oylcarbamoylmethyl)iminodiacetic acid, 3a: 7a: 12a: trihydroxy-24-norchol anyl-23-iminodiacetic acid, N-(3-bromo-2,4,6-trimethylphenylcarbamoylmethyl) iminodiacetic acid, benzimidazole methyliminodiacetic acid, N-(3-cyano-4,5-dimethyl-2-pyrryl-carbamoylmethyl) iminodiacetic acid, ethylenediamine-N,N-bis(-2-hydroxy-5-bromo-phenyl) acetate, N'acyl and N'-sulfonyl ethylene diamine-N,N diacetic acid; N'-acetyl EDDA, N'-benzoyl EDDA, N'-(p-toluenesulfonyl) EDDA, N'-(P-t-butylbenzoyl) EDDA, N'-(benzenesulfonyl) EDDA, N'-(p-chlorobenzenesulfonyl) EDDA, N'(p-ethylbenzenesulfonyl) EDDA, N'-(p-n-propylbenzenesulfonyl) EDDA, N'-(naphthalene-2-sulfonyl) EDDA, N'-(2,5-dimethylbenzenesulfonyl) EDDA; N-(2-acetylnaphthyl) iminodiacetic acid; N-(2-naphthyl)methyl)iminodiacetic acid; rose bengal, congo red, bromosulphthalein, bromophenol blue, phenolphthalein, toluidine blue, indocyanine green, iodipamide, ioglycamic acid, bilirubin, cholyglycyliodohistarnine, thyroxineglucuronide, penicillamine, β-mercaptoisobutyric acid, dihydroehioctic acid, 6-mercaptopurine, kethoxal-bis(thiosemicarbazone); 1-hydrazinophthalazine(hydralazine)-sulfonyl urea; pyridoxylidene glutamate, pyridoxylidene isoleucine, pyridoxylidene phenylalanine, pyridoxylidene tryptophan, pyridoxylidene 5-methyl tryptophan; 3-hydroxy-4-formyl-pyridene glutamic acid; tetracycline, 7-carboxy-β-hydroxyquinoline, phenolphthalexon, eosin and verograffm.

Optionally, the liposomal construct is also provided with a masking agent in imtimate association therewith to protect it from immunoreactive attack, such as by macrophages.

A preferred embodiment of the invention then provides a liposomal construct for delivering serotonin or a serotonergic agonist to the liver of a mammal comprising a liposomal carrier, serotonin or a serotonergic agonist entrapped within or associated with said liposomal carrier, a biliary-attracted molecule bound to the surface of the liposomal carrier for binding to a hepatobiliary receptor in the liver, and a sequestering agent within said liposomal carrier in an amount effective to reduce leakage of the serotonin or liposomal membrane. Optionally, the liposomal construct includes a masking agent in intimate association therewith to protect it from immunoreactive attack.

Also provided are pharmaceutical compositions of the liposomal constructs for inducing a serotonergic response in the liver of a mammal comprising a liposomal carrier; serotonin or a serotonergic agonist entrapped within or associated with said liposomal carrier a targeting moiety bound to the surface of said liposomal carrier; wherein said targeting moiety comprises a biliary-attracted molecule which binds to a hepatobiliary receptor in the liver; a sequestering agent distributed within said liposomal carrier, said sequestering agent being present in an amount effective to reduce leakage of the serotonin or serotonergic agonist from the liposomal construct prior to delivery to the liver, a masking agent to protect said liposomal carrier from immunoreactive attack, and a pharmaceutically acceptable excipient.

The liposomal constructs and pharmaceutical compositions of this invention are useful for the treatment of disease states responsive to biogenic amines. Such disease states may include, for example, hypertension, shock, cardiac failure, arrhythmias, asthma, allergy, anaphylaxis and diabetes.

This invention is particularly useful for delivery of biogenic amines, which as potent neurotransmitters, should be sequestered tightly within a liposomal construct in order to minimize or substantially eliminate interactions with receptors of organs or tissues other than those targeted by the construct. Biogenic amines include sympathomimetic amines, i.e., naturally occurring catecholamines and drugs that mimic their action, and autacoids that act at serotonin receptors to elicit an hepatic glucose storage response. See Goodman and Gilman, *The Pharmacological Basis of Therapeutics*, 9th ed., Macmillan Publishing Company (1995). Such neurotransmitters are water-soluble and exhibit a polar nature in keeping with their ability to migrate through liposomal membranes. Also of importance is the fact that the quarternary amines, such as epinephrine and acetylcholine, manifest a positive charge over a broad pH range, while the remaining neurotransmitters are categorized as primary amines and only produce a full positive charge at physiological pH and below.

Because biogenic amines evidence a pronounced polarity contributed by a positively charged quaternary amine or a positively charged primary amino group at physiological pH, they demonstrate unusual water-activity and are capable of transversing liposomal membranes. They are thus difficult to retain for any period of time within a liposomal core volume. The retention of biogenic amines within a liposomal construct is required not only due to their primary functions, but also because they can and do act in vivo as neurotransmitters. Biogenic amines interact with and are contained in many different cell types including those that are not necessarily associated with the cell or organ to which it is intended to deliver the active agent. These cells include neurons, platelets, mast cells and enterochromaffm cells, etc. Therefore, if a biogenic amine, which has been incorporated in a liposome, is not strongly sequestered or retained by the liposomal structure, then it may leak from the liposomes and elicit undesirable pharmacological responses with other cell types that manifest the same receptors.

It is also desirable to utilize a "targeted" liposomal carrier with the present invention. Such targeting can be accomplished by means of the incorporation of antibodies, lectins, peptides, proteins, carbohydrates, glycoproteins, hepatobiliary specific agents and the like on the surface of the liposomes.

This invention provides several modalities by which biogenic amines can be effectively retained or associated with a liposomal construct for an extended time period in order to prevent their leakage to the external liposomal environment during storage and delivery to a host. In one embodiment of the invention, a sequestering agent may be used that is contained within the core volume of the liposome. In an alternative embodiment, a sequestering agent may be used that is a component of the liposomal carrier's membrane. Suitable sequestering agents are nucleotide derivatives, negatively charged derivatives of dicarboxylic acids, e.g. polyamino acid polymers and copolymers, such as the amino acid copolymer poly(glutamic-aspartic acid). Also, polyphosphate polymers, phosphate derivatives and phosphatidyl phosphate compounds may be used to sequester biogenic amines within a liposomal core volume.

Phosphatidyl phosphate derivatives such as phosphatidic acid and phosphatidyl polyphosphate derivatives such as phosphatidyl di- and triphosphate and phosphatidylinositol 4,5-diphosphate when incorporated as essential constituents of the phospholipid liposomal membrane provide a distribution of anionic charge to the inner and outer membrane surfaces that not only facilitates the sequestration of biogenic amines, but also provides surface charge repulsion between neighboring liposomal carriers. Any biogenic amines that become externally sequestered to the liposomal surface can be removed easily by employing ion-exchange chromatography.

Other members of the class of polyphosphate compounds which have found use as sequestering agents for biogenic amines within a liposomal construct include phytic acid, the hexaphosphate of inositol, and phosvitin, a protein derivatized with phosphate which manifests a phosphate functional group esterified to a serine residue at approximately every third amino acid.

A particular application of this invention can be illustrated with the hormone and neurotransmitter serotonin.

The leakage of a biogenic amine such as serotonin from a liposomal carrier can elicit untoward biochemical and physiological side-effects since the unsequestered neurotransmitter has the potential to interact with cellular receptors that are not designated for activation. Thus liposomal leakage of serotonin increases the likelihood of unwanted neurohormonal binding or uptake, as well as neurotransmission.

In earlier studies, such as described in U.S. Pat. No. 4,761,287, it has been shown that in order to adequately treat non-insulin dependent diabetes mellitus (Type II), it is necessary to deliver the hormone serotonin to the cellular hepatocytes in the liver using a targeted liposomal construct. The delivery of this hormone, in conjunction with the hormone insulin, signals the liver to store blood glucose as glycogen. This action results in the reduction of the high circulating levels of glucose and lessens exposure of other tissues and organs in the body to high glucose levels. If the hormone were to leak from its carrier, it would be difficult to deliver the correct dosage form to the liver and the intended use of the targeted delivery system would be compromised.

Therefore, in a preferred embodiment, this invention is directed to the retention of biogenic amines such as serotonin or serotonergic agonists within a targeted liposomal construct. If exogenous serotonin, which has been incorporated in a liposome, is not strongly sequestered or retained by the liposomal structure, then there is a possibility that serotonin could leak from the liposomes and elicit undesirable pharmacological responses with other cell types that manifest serotonin receptors.

In an especially preferred embodiment, the incorporation of the nucleotide adenosine 5'-triphosphate (ATP) in a liposomal core volume facilitates and augments trapping or sequestration of biogenic amines. Of particular interest is an ATP-serotonin complex.

Because of the complexity of the multiplex structure of a liposomal carrier, a biogenic amine, a sequestering agent, and, optionally, a targeting molecule, the specific chemical interaction between the nucleotide trapping agent and positively charged amines remains undetermined.

It is speculated that within the liposomal construct a complex is formed, for example, between ATP and serotonin. This association is thought to be mediated through the positively charged terminal amino group on serotonin which ionically links with the negatively charged phosphate groups on ATP resulting in a paired-charge interaction at physiological pH forming a complex with four serotonins per ATP. Other nucleotides may be used, as described above.

In addition to nucleotide compounds, amino acid polymers, such as of the dicarboxylic acids aspartic acid and glutamic acid, have been determined to sequester biogenic amines within a liposomal construct. The copolymeric structure of aspartic acid covalently linked to glutamic acid creates an anionic sink that can bind biogenic amines such as serotonin.

The liposomal constructs of this invention provide useful agents for pharmaceutical applications for administering an active agent to a host. Accordingly, the constructs of this invention are useful as pharmaceutical compositions in combination with pharmaceutically acceptable carriers. Administration of the constructs described herein can be via any of the accepted modes of administration for the biologically active substances that are desired to be administered. These methods include oral, topical, parenteral, ocular, transdermal, nasal and other systemic or aerosol forms.

Depending on the intended mode of administration, the compositions used may be in the form of solid, semi-solid or liquid dosage forms, such, as for example, tablets, suppositories, pills, capsules, powders, liquids, suspensions, or the like, preferably in unit dosage forms suitable for single administration of precise dosages. The pharmaceutical compositions will include the liposomal construct as described and a pharmaceutical acceptable excipient, and, optionally, may include other medicinal agents, pharmaceutical agents, carriers, adjuvants, etc.

Topical formulations composed of the liposomal constructs hereof, penetration enhancers, and other biologically active drugs or medicaments may be applied in many ways. The solution can be applied dropwise, from a suitable delivery device, to the appropriate area of skin or diseased skin or mucous membranes and rubbed in by hand or simply allowed to air dry. A suitable gelling agent can be added to the solution and the preparation can be applied to the appropriate area and rubbed in. Alternatively, the solution formulation can be placed into a spray device and be delivered as a spray. This type of drug delivery device is particularly well suited for application to large areas of skin, to highly sensitive skin or to the nasal or oral cavities.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolaine oleate, etc.

The amount of active compound administered will of course, be dependent on the subject being treated, the type and severity of the affliction, the manner of administration and the judgment of the prescribing physician. In addition, if the dosage form is intended to give a sustained release effect, the total dose given will be integrated over the total time period of the sustained release device in order to compute the appropriate dose required. Although effective dosage ranges for specific biologically active substances of interest are dependent upon a variety of factors, and are generally known to one of ordinary skill in the art, some dosage guidelines can be generally defined. For most forms of administration, the lipid component will be suspended in an aqueous solution and generally not exceed 30% (w/v) of the total formulation. The drug component of the formulation will most likely be less than 20% (w/v) of the formulation and generally greater than 0.01% (w/v)

In general, topical formulations are prepared in gels, creams or solutions having an active ingredient in the range of from 0.001% to 10% (w/v), preferably 0.01 to 5%, and most preferably about 1% to about 5%. (Of course, these ranges are subject to variation depending upon the potency of the biogenic amine, and could in appropriate circumstances fall within a range as broad as from 0.001% to 20%.) In all of these exemplary formulations, as will other topical formulations, the total dose given will depend upon the size of the affected area of the skin and the number of doses per day. The formulations can be applied as often as necessary, but preferably not more than about 3 times per day.

For oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include solutions, suspensions, tablets, dispersible tablets, pills, capsules, powders, sustained release formulations and the like.

Preferably the compositions will take the form of a pill or tablet. Thus the composition will contain along with the active ingredient: a diluent such as lactose, sucrose, dicalcium phosphate, or the like; a lubricant such as magnesium stearate or the like; and a binder such as starch, gum acacia, gelatin, polyvinylpyrolidine, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, etc. Actual methods of preparing such dosage forms are known, or will be apparent, to those skilled in this art; for example, see *Remington: The Science and Practice of Pharmacy*, 19th ed., 1995 (Mack Publishing Co., Easton, Pa.). The composition or formulation to be administered will, in any event, contain a quantity of the active compound, e.g., serotonin, in an amount sufficient to effectively treat the disorder or disease of the subject being treated.

Dosage forms or compositions containing active ingredient in the range of 0.005% to 5% with the balance made up from non-toxic carrier may be prepared. The exact composition of these formulations may vary widely depending on the particular properties of the drug in question. However, they will generally comprise from 0.01% to 5%, and preferably from 0.05% to 1% active ingredient for highly potent drugs, and from 2–4% for moderately active drugs.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain rninor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 5% in solution are employable, and will be higher if the composition is a solid which will be subsequently diluted to the above percentages. Preferably the composition will comprise 0.2–2% of the active agent in solution.

Nasal solutions of the liposomal construct alone or in combination with pharmaceutically acceptable excipients can also be administered.

Formulations of the liposomal construct may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

Leakage from prepared liposomes containing a biogenic amine and a sequestering agent can be determined from conventional stability testing, both in a controlled storage environment approximating storage conditions, and in physiological fluids, depending upon the intended mode of delivery of the liposomal construct.

Depending on the particular application, lipids can be produced and loaded by the methods disclosed herein, and those methods described in U.S. Pat. Nos. 4,946,787; 4,603,044; and 5,104,661, and the references cited therein. Typically, the aqueous liposomal formulations of this invention will comprise 0.01% to 10% active agent by weight (i.e.,100 mg drug per ml), and 1% to 20% lipid by weight comprising a sequestering agent in a quantity of 1% to 100% of this lipid component by weight, and an aqueous solution, optionally containg salts and buffers, in a quantity to make 100% by volume. Particularly preferred are formulations which comprise 0.1% to 5% active agent and a lipid component comprising a sequestering agent in a quantity of 50% or more by weight of the lipid component. Most preferred is a formulation comprising 1% to 5% active agent by weight, up to 20% by weight of a lipid component, in turn comprising 10% to 100% by weight of a sequestering agent and an amount of aqueous solution sufficient (q.s.) to make 100% by volume. In all such formulations, it is desirable to have a charge ratio of sequestering agent to biogenic amine of at least 1:1. Most preferably, there is at least 50% greater residual charge (polymer or non-polymer) versus biogenic amine, to ensure sufficient sequestering efficiency.

EXAMPLE 1

Preparation of Hepatocyte-directed Liposomes Containing a Serotonin-ATP Complex.

Adenosine 5'-triphosphate (ATP) is used as a liposomal sequestrant for serotonin along with the lipid membrane constituents of 69.0 mg of 1,2-distearoyl-sn-glycerol-3-phosphatidylcholine (distearoyl lecithin) and 14.0 mg of dicetylphosphate both from Avanti Biochemicals; 1.0 mg of N-(2,6-diisopropylphenylcarbamoylmethyl)imino diacetic acid and 5.0 mg of cholesterol, both from Sigma Chemical Co. The lipid constituents are solubilized in 1.5 ml of chloroform:methanol solvent (2:1 v/v) from Aldrich Chemical Co. The sample is placed on a Büchi Rotoevaporator and taken to dryness with slow turning under aspirator vacuum at 60° C. Then a solution of 2.4 ml of freshly prepared 40 mM sodium phosphate buffer at pH 7.4 containing 4.2 mg/ml human serum albumin, 10 mg/ml serotonin and at least 14.4 mg/ml of ATP, all from Sigma Chemical Co., is prepared and added to the dried lipid components. The sample is sonicated at setting #4 for 15 minutes at 60° C., using a HeatSystems Ultrasonic/Cell Disrupter equipped with a transducer and cup horn. Next, the sample is annealed at 60° C. with slow turning for 15 minutes to permit the liposomal membranes to become more perfectly formed and more stable. The sample is then centrifuged in a Triac Clinical Centrifuge at the blood setting for 15 minutes at room temperature, and then 1.5 ml of the supernatant material is chromatographed on a 1.5×25.0 cm Sephadex G-100-120 column that has been equilibrated with 40 mM phosphate buffer pH 7.4. This first chromatography is performed to remove the unentrapped serum albumin and the serotonin-ATP complex. The liposomes are collected and, with respect to the initial concentration on N-(2,6-diisopropylphenylcarbamoylmethyl)imino diacetic acid, they are reacted with a five-fold mole excess of chromium chloride hexahydrate. The purified liposomes containing the serotonin ATP complex were then reacted with a five-fold mole excess of N-(2,6-diisopropylphenylcarbamoylmethyl) imino diacetic acid target molecules. The liposomes are then again rechromatographed using the same buffer to remove unreacted target molecules. The liposomes were stored under nitrogen at 5° C. These hepatocyte-directed liposomes containing the serotonin-ATP complex are diluted with 40 mM phosphate-buffered saline, pH 7.4, prior to the administration to a warm-blooded host.

The liposomes are not expected to exhibit leakage of serotonin during storage under normal conditions prior to delivery to a host animal. Furthermore, the liposome constructs are not expected to exhibit any significant leakage when maintained in a solution at physiological pH for time periods approximating the times for demonstration of a physiological effect of serotonin at the liver in the studies described in U.S. Pat. No. 4,603,044. The liposome constructs may be delivered to a host in the manner described in U.S. Pat. No. 4,603,044 and are expected to demonstrate activity in the tests described.

EXAMPLE 2

High Pressure Liquid Chromatography (HPLC) Methods.

Alltech HPLC system with UV detection at 230 nm was used in the following chromatography experiments. The mobile phase was 5 mM triethylamine pH 4.5 with acetic acid 90% (v/v) acetonitrile 10% (v/v). The flow rate was 1.0 ml/min. Standard curves from 0–100 ppm to 0–0.01 ppm using injection volumes of 10 μl and 100 μl were developed. All curves showed linear response.

EXAMPLE 3

16-Hour Passive Loading of 5-hydroxytryptamine Creatinine Sulfate (5-HT CS) Into Liposomes, Followed by a Leak Rate Study.

5-hydroxytryptamine creatinine sulfate (5-HT CS) stock was made up at 1.0 mg/ml (2.58 mM). HDV-D198A is a mixture of lipid constituents dried to an amorphous crust and comprising distearoyl lecithin (DSL), cholesterol (CHOL), dicetyl phosphate (DCP), and Cr-(bis)-[N-(2,6-diisopropylphenylcarbamoylmethyl) iminodiacetic acid] (Crystal). (Vesicles formed from HDV-D198A are hepatocyte-directed vesicles (HDV).) HDV-D198A was added at 1.3 mg lipid/ml to the 5-HT CS solution and passively loaded for 16 hrs. Four chromatography runs were performed using 20 mM $PO_4$ buffer pH 7.0 and PD 10 columns. All fractions were pooled. HPLC analysis was performed on fractions and the most concentrated tubes were used for study. Tube #5 was used and had 24.7 μg/ml of 5-HT CS associated with the liposomal fraction. The results are shown in the following table:

| Time | Retention μg of 5-HT CS in lipid fraction | % of total μg retained |
|---|---|---|
| 2 hrs | 21.7 μg | 88.0 |
| 4 hrs | 19.1 μg | 77.0 |
| 18 hrs | 17.7 μg | 73.4 |

EXAMPLE 4

Active Loading of ATP with Liposomes.

3.6 mg/ml ATP (6.5 mM) in 20 mM $PO_4$ buffer pH 7.0 with 14.15 mg/ml HDV-D198A and 50 μl $^{14}$CATP were actively loaded with 1.5 min sonication at 60° C. after 30 min hydration at 60° C. 1.0 ml of the sample was chromatographed over a Sepharose CL-6B column and 1.5 ml fractions were collected.

Results: 24.8 μg of ATP was found in 11 tubes containing the lipid fractions.

Total ATP recovered was 92.7%.

% of ATP associated with liposomal fraction was 0.7%.

EXAMPLE 5

Passive Loading of 5-Hydroxytryptamine Hydrochloride (5-HT HCl) into Liposomes Followed by a Leak Rate Study at 2, 16, 40 and 60 Hours Using Blank Presonicated Liposomes.

10.0 ml of stock HDV-D198A was prepared at 28.3 mg/ml and hydrated at 60° C. for 30 min. The sample was then sonicated in 1.0 ml aliquots for 1.0 min at 60° C. size=79.6 nm. A stock solution of 6.0 mg/ml 5-hydroxytryptamine hydrochloride (5-HT HCl) was prepared and added to the lipid preparation. Equal volumes of 5-HT HCl and lipid were used. Therefore, final concentrations were 14.15 mg/ml HDV and 3 mg/ml 5-HT HCl (14.1 mM). The sample was passively loaded for 16 hours.

Size after mixing=132.5 nm 123.4 μg of 5-HT HCl or 4.11% was found in total lipid fraction.

Tubes #8 and #9 were pooled for the leak rate study. 55.7 μg 5-HT HCl/ml found in pooled sample of Tubes #8 and #9.

Four chromatography runs were performed using 1.0 ml aliquots. A Sephadex G25 short column was equilibrated with 10 mM 4-(2-hydroxyethyl)-1-piperazineethane sulfonic acid (HEPES) buffer pH 7.0.

The 55.7 μg 5-HT HCl/ml of the pooled sample of Tubes #8 and #9 was used to study the leak rate as a function of time. The results are shown in the following table:

| Time | Retention μg 5-HT HCl in lipid fraction | % of total μg still retained |
|---|---|---|
| 2 hr | 31.2 | 68.7% |
| 16 hr | 31.1 | 53.3% |
| 40 hr | 22.7 | 45.9% |
| 64 hr | 23.1 | 47.0% |

EXAMPLE 6

Leak Rate Study of 5-HT HCl at 2.0 mg 5-HT HCl/ml (9.45 mM) with Lipid Concentration at 14.15 mg Lipid/ml Using 10 mM 4-(2-Hydroxyethyl)-1-Piperazineethane Sulfonic Acid (HEPES) Buffer pH 7.0.

56.6 mg of HDV-D198A was hydrated in 2.0 ml of 10 mM HEPES buffer pH 7.0 at 60° C. for 30 min. The concentration of the lipid stock was 28.8 mg lipid/ml.

8.0 mg 5-HT HCl was dissolved in 1900 μl of 10 mM HEPES buffer pH 7.0. 100 μl $^{14}$C 5-HT CS was added to make a total volume of 2.0 ml total volume. The concentration of the 5-HT HCl stock was 4.0 mg 5-HT HCl/ml.

A 500 μl aliquot of lipid stock and a 500 μl of 5-HT HCl stock was added and mixed and sonicated for 1.0 min at 60° C. in polycarbonate tubes. The final concentrations were 2.0 mg 5-HT HCl/ml (9.4 mM) and 14.15 mg lipid/ml.

Three separate 1.0 ml aliquots of sonicated sample were chromatographed over a Sephadex G25 short column. The tubes were pooled and radiochem analysis performed. The results are shown in the following table:

| Retention μg 5-HT HCL in lipid fraction | % of total μg 5-HT HCL retained in lipid fraction | μg 5-HT HCl in free pool | % of 5-HT HCL in free pool | % of total 5-HT HCL recovered following chromatography |
|---|---|---|---|---|
| 300 | 15.0% | 1564 | 78.2% | 93.2% |

Tube #4 was used for a leak rate study and had an initial concentration of 84.5 μg 5-HT HCl/ml. 1.0 ml was chromatographed over a Sephadex G25 short column at selected times to determine leak rate. The results are shown in the following table:

| | Time | Retention μg 5-HT HCl in lipid fraction | % of total μg 5-HT HCL retained in lipid fraction | μg of 5-HT HCl in free pool | % 5-HT HCl in free pool | % of total 5-HT HCl recovered following chromatography |
|---|---|---|---|---|---|---|
| 112A | 2 hrs | 67.5 | 79.0% | 10.8 | 12.7% | 92.0% |
| 112B | 20 hrs | 54.3 | 65.2% | 23.0 | 27.6% | 92.8% |
| 112C | 44 hrs | 49.2 | 60.4% | 25.7 | 31.5% | 91.9% |

Tube #4 from the t=20 sample in the table above was chromatographed over a Sephadex G25 short column to see if 5-HT remains associated with lipid. Initial analysis of tube #4 revealed 19.2 μg of 5-HT HCl/ml. The results after chromatography are shown in the following table:

| Retention μg 5-HT HCL in lipid fraction | % of total μg of 5-HT HCl retained in lipid fraction |
|---|---|
| 16.8 | 87.5% |

EXAMPLE 7

Incorporating 5-HT HCl into Liposomes Using the M-110 Microfluidizer.

1.0613 gm HDV-D198A was hydrated in 37.5 ml of 10 mM HEPES buffer pH 7.0 (28.3 mg/ml) at 60° C. for 30 min using a Buichi Rotoevaporator. 150 mg 5-HT HCl was dissolved in 37.5 ml 10 mM HEPES buffer pH 7.0 (4.0 mg/ml). 5-HT HCl stock was added to the lipid stock and mixed at 60° C. for 5 min to bring to temperature. The fluidizer was pre-heated with 150 ml 60° C. deionized and 0.2 μm filtered milli Q water and shear pressure was set to 14000 psig. 5-HT lipid mix was passed through fluidizer twice at 12000 psig shear pressure and 60 psig head pressure. The preparation was filtered through 0.2 μm acrocap filter using sterile technique. The sarnple passed through the filter without difficulty. The final concentration of 5-HT HCl was 2.0 mg/ml (9.4 mole/ml). The final concentration of HDV was 14.15 mg/ml. The preparation appears translucent with slight blue tint. Characteristics of this preparation are shown in the following table:

| Size | pH | retention µg of 5-HT HCl in lipid fraction | % of total µg 5-HT HCl retained in lipid fraction | µg of 5-HT HCl in free pool | % 5-HT HCl in free pool | % of total 5-HT HCl recovered following chromatography |
|---|---|---|---|---|---|---|
| 76.4 nm | 6.0 | 242 µg | 13.2% | 1504 | 82.1% | 95.4% |

Additional leak rate studies were done using pooled lipid fractions from the initial chromatographies containing 80–82 µg 5-HT HCl/ml The results of these studies are shown in the following table:

| time | retention µg of 5-HT HCl in lipid fraction | % of total µg 5-HT HCl retained in lipid fraction | µg of 5-HT HCl in free pool | % 5-HT HCl in free pool | % of total 5-HT HCl recovered following chromatography |
|---|---|---|---|---|---|
| 2 hrs | 76 | 94.8 | 22.1 | 27.2 | 122 |
| 20 hrs | 56 | 68.3 | 33.8 | 41.2 | 109.5 |
| 68 hrs | 59.3 | 72.2 | 33.8 | 41.1 | 113 |
| 92 hrs | 65 | 71.5 | 39 | 42.9 | 114 |
| 116 hrs | 61 | 70.1 | 18 | 20.6 | 90.7 |
| 140 hrs | 50 | 59.9 | 36.9 | 44.2 | 104 |

EXAMPLE 8

Replacement of Dicetyl Phosphate (DCP) in the HDV Liposome Formulation with Phosphatidic Acid (PA).

|  | DSL | CHOL | PA | Crystal |
|---|---|---|---|---|
| MW | 790 | 386.7 | 449 | 748 |
| mg | 40.8 | 5.2 | 12.5 | 0.7 |
| µmoles | 51.6 | 13.4 | 27.8 | 0.94 |

Lipids were dissolved in chloroform:methanol (1:1 v/v) and dried under high vacuum for 1 hour. The dried crust was hydrated with 2.0 ml of 10 mM HEPES pH 7.0 buffer for 60 min at 60° C. to prepare lipid Stock A. 20.0 mg of 5-HT HCl was dissolved in 5.0 ml 10 mM HEPES buffer pH 7.0 to prepare 5-HT Stock B. 500 µl lipid Stock A was combined with 500 µl 5-HT HCl Stock B and pipetted into polycarbonate tubes and sonicated at 60° C. for 1.0 min.

Final concentrations:

5-HT HCl=2.0 mg/ml (9.4 mol/ml)

HDV=14.15 mg/ml

Size=70.9 pH of fmal prep=6.2

1.0 ml was chromatographed over a PD-10 column equilibrated in 10 mM HEPES buffer pH 7.0. Tubes 1–6 were pooled comprising the lipid fractions. Tubes 7–30 were pooled comprising the free pool of 5-HT HCL. The results obtained for this liposomal construct are shown in the following table:

| retention µg of 5-HT HCl in lipid fraction | % of total µg 5-HT HCl retained in lipid fraction | µg of 5-HT HCl in free pool | % 5-HT HCl in free pool | % of total 5-HT HCl recovered following chromatography |
|---|---|---|---|---|
| 205 µg | 10.25% | 1723 | 86.2% | 96.4% |

Tube 4 from the initial chromatography was then chromatographed over a PD-10 column after 24 hours incubation at ambient temperature. The sample initially contained 102 µg 5-HT HCl/ml.

| retention µg of 5-HT HCl in lipid fraction | % of total µg 5-HT HCl retained in lipid fraction | µg of 5-HT HCl in free pool | % 5-HT HCl in free pool | % of total 5-HT HCl recovered following chromatography |
|---|---|---|---|---|
| 67 µg | 65.7% | 32 | 31.3% | 97.0% |

EXAMPLE 9

Experiment with Phosvitin to Enhance 5-HT HCl Association with the Liposomal Fraction.

56.6 mg HDV-D198A was added to 25 ml round-bottom flask and hydrated with 2.0 ml 10 mM HEPES buffer pH 7.0 at 60° C. for 30 min to obtain a lipid Stock A. 15.6 mg Phosvitin plus 20.0 mg 5-HT HCl were dissolved in 5 ml of 10 mM HEPES buffer pH 7.0 total volume to prepare Stock B. 500 µl lipid Stock A plus 500 µl Stock B were sonicated for 1.0 min at 60° C.

Final concentrations:

Lipid: 14.15 mg/ml

5-HT HCl: 2.0 mg/ml (9.4 mol/ml)

Phosvitin: 1.6 mg/ml (9.4 mol/ml)

size=140.8 nm pH=6.5

1.0 ml of the fmal preparation was chromatographed over a PD-10 column equilibrated in 10 mM HEPES buffer pH 7.0. The results of this experiment are shown in the following table:

| retention µg of 5-HT HCl in lipid fraction | % of total µg 5-HT HCl retained in lipid fraction | µg of 5-HT HCl in free pool | % 5-HT HCl in free pool | % of total 5-HT HCl recovered following chromatography |
|---|---|---|---|---|
| 80 µg | 4.0% | 1512 | 75.6% | 79.6% |

EXAMPLE 10

Experiment with Poly (α Glutamic:α Lysine): Mole Ratio 60:40, MW 23,000.

The molecular weight of glutamic/lysine residue was 293.3 (used to calculate molarity of Glu). 56.6 mg HDV-D198A was hydrated in 2.0 ml 10 mM HEPES buffer pH 7.0 at 60° C. for 30 min to prepare lipid Stock A. 4.0 mg 5-HT HCl plus 3.0 mg poly (Glu-Lys) dissolved in 2.0 ml 10 mM HEPES buffer pH 7.0 for Stock B. 500 µl lipid Stock A plus 500 µl Stock B were sonicated for 1.0 min at 60° C. in polycarbonate tubes.

Final concentrations:
Lipid: 14.15 mg/ml
5-HT HCl: 9.4 µ moles/ml
5-HT: 2.0 mg/ml
PolyGlu: 1.5 mg/ml
PolyGlu: 5.1 µ moles/ml
Size=117 nm, pH=6.4.

1.0 ml of the final preparation was chromatographed over a PD-10 column in 10 mM HEPES buffer pH 7.0. The results are shown in the following table:

| retention µg of 5-HT HCl in lipid fraction | % of total µg 5-HT HCl retained in lipid fraction | µg of 5-HT HCl in free pool | % 5-HT HCl in free pool | % of total 5-HT HCl recovered following chromatography |
|---|---|---|---|---|
| 194 µg | 9.7% | 1650 | 82.5% | 92.2% |

The chromatogramn of 5-HT HCl in lipid peak was symmetrical.

Tube 4 from initial chromatography containing 106 µg 5-HT HCl/ml and Poly(Glu-Lys) was chromatographed after 24 hours incubation at ambient temperature 1.0 ml from tube 4 was chromatographed over a PD-10 column in 10 mM HEPES buffer pH 7.0 after 24 hrs incubation at ambient temperature. The results are shown in the following table:

| retention µg of 5-HT HCl in lipid fraction | % of total µg 5-HT HCl retained in lipid fraction | µg of 5-HT HCl in free pool | % 5-HT HCl in free pool | % of total 5-HT HCl recovered following chromatography |
|---|---|---|---|---|
| 64 µg | 60.4% | 40 | 37.7% | 98.1% |

EXAMPLE 11

Passive-Loading of 6.5 mM 5-HT CS and Passive-Loading of 6.5 mM ATP Na$_2$.

20 mM PO$_4$ buffer pH 7.0 was used for the loading step. The ATP concentration was 3.6 mg/ml (6.5 mM).

The 5-HT CS concentration was 2.5 mg/ml (6.5 mM).

The HDV liposome concentration was 1.06 mg lipid/ml (750 µl of 14.15 mg/ml in 10 ml).

25 mg 5-HT and 35.8 mg ATP to 10 ml 20 mM PO$_4$ buffer pH 7.0 were added. 750 µl of liposomes was added to 10 ml of solution and incubated at room temperature for 97 hours. One ml of solution was chromatographed over a 10DG column (1.5×11.5 cm). One ml fractions were collected. The most concentrated fraction (tube 5) was retained for further time studies.

Time 0: 1st Chromatography—22.8 µg 5-HT CS loaded or 22.8 µg of 5-HT CS÷2,500 µg of 5-HT CS×100= 0.91% associated with the liposomal fraction Time 3.5 hrs: 2nd Chromatography—87% retained (11.4 µg out of 13.1 µg in tube 5)

Time 16 hrs: 52% retained (6.8 µg out of 13.1 µg in tube 5)

EXAMPLE 12

Active-loading of 1.0 mM and Active-loading of 3.0 mM 5-HT HCl.

10 mM HEPES buffer pH 7.0 was used. The ATP concentration was 0.55 mg/ml (1 mM). The 5-HT HCl concentration was 0.65 mg/ml (3 mM). The liposome concentration was 14.15 mg/ml. The cholesterol ($^{14}$C) Oleate concentration was 50 µl.

28.3 mg of HDV-D 198A was added to 50 µl of Cholesterol ($^{14}$C) Oleate that had been dried under vacuum in a 25 ml round-bottom flask to evaporate off the toluene. Lipids were dissolved in 1.0 ml of chloroform:methanol (2:1 v:v) and then hydrated with 2 ml HEPES buffer. The final lipid concentration was 14.15 mg/ml.

The mixture, one ml at a time, was sonicated for 30 seconds and then 1.0 ml of the ATP 5-HT solution was slowly added while sonicating for another 60 seconds. Three 1.0 ml aliquots were separated on a CL-6B Sepharose column (2×20 cm). The two most concentrated fractions were pooled. Chromatography after Time 0 performed on a PD-10 column (1.5×5.5 cm) and collected in 1.0 ml fractions.

Time 0: 1st Chromatography—18 µg 5-HT HCl loaded or 2.8% of total (0.65 mg/ml), 576 µg free and 1.5 µg of 5-HT HCl found in ATP fraction (92% accounted for)

Time 3.5 hrs: 2nd Chromatography—108% retained (0.55 µg out of 0.51 µg in pool)

particle size: 110 nm after 1 hour

While the invention has been described with respect to the specific embodiments described herein, it is understood that modifications thereto and equivalents and variations thereof will be apparent to one skilled in the art and are intended to be and are included within the scope of the claims appended hereto.

What is claimed is:

1. A liposomal construct for delivering a diagnostic or therapeutic agent to a mammal comprising:

a) a liposomal carrier;

b) a diagnostic or therapeutic agent comprising a biogenic amine selected from the group consisting of L-β-3, 4dihydroxyphenylanine, 3-(2-aminoethyl)-5-hydroxyindole, 2-(4-imidazolyl)ethylamine, 4-[1-hydroxy-2-[(methylamino)]ethyl]-1,2-benzenediol, 1-[3,4-dihydroxyphenyl]-2-aminoethanol, γ-amino-n-butyric acid and acetylcholine, entrapped within or associated with said liposomal carrier; and c) a separate sequestering agent selected from the group consisting of a nucleotide derivative selected from the group consisting of adenosine 5'-triphosphate (ATP), cytidine 5'-triposphate(CTP), guanosine 5'-triphosphate (GTP), thymidine 5'triphosphate (TTP), uridine 5'-triphosphate (UTP), adenosine 5'-diphosphate (ADP), cytidine 5'-diphosphate (CDP), guanosine 5'-diphosphate (GDP), thymidine 5'-diphosphate (TDP), uridine 5'-diphosphate (UDP), adenosine 5'-monophosphate (AMP),cytidine 5'-monophosphate (CMP), guanosine 5'-monophosphate (GMP), thymidine 5'-mononhosphate (TMP), uridine 5'-monophosphate (UMP), adenosine 5'-tetraphosphate, guanosine 5'-tetraphosphate and thymidine 5'-tetraphosphate, a polyphosphate derivative selected from the group consisting of phytic acid and the hexaphoshate of inositol and phosvitin, and an amino acid polymer, distributed within said liposomal carrier, said sequestering agent being present in an amount effective to reduce leakage of the diagnostic or therapeutic agent from the liposomal construct prior to delivery and being in addition to said diagnostic or therapeutic agent.

2. A liposomal construct of claim 1 further comprising a targeting moiety associated with the surface of said liposomal carrier; wherein said targeting moiety binds to a receptor associated with a targeted situs.

3. A liposomal construct of claim 1 wherein the biogenic amine is selected sympathomimetic amine or an autacoid.

4. A liposomal construct for delivering a diagnostic or therapeutic agent to a mammal comprising:
   a) a liposomal carrier;
   b) a diagnostic or therapeutic agent selected from the group consistincg of serotonin and serotonergic agonists entrapped within or associated with said liposomal carrier; and
   c) a separate sequestering agent selected from the group consisting of a nucleotide derivative selected from the group consisting of adenosine 5'triphosphate (ATP), cytidine 5'-triphosphate (CTP), guanosine 5'-triphosphate (GTP), thymidine 5'-triphosphate (TTP), uridine 5'-triphosphate (UTP), adenosine 5'-diphosphate (ADP), cytidine 5'-diphosphate (CDP), guanosine 5'-diphosphate (GDP), thymidine 5'-diphosphate (TDP), uridine 5'-diphosphate (UDP), adenosine 5'-monophosphate (AMP), cytidine 5'-monophosphate (CMP), guanosine 5'-monophosphate (GMP), thymidine 5'-monophosphate (TMP), uridine 5'-monophosphate (UMP), adenosine 5'-tetraphosphate, guanosine 5'-tetraphosphate and thymidine 5'-tetraphosphate, a polyphosphate derivative selected from the group consisting of phytic acid and the hexaphosphate of inositol and phosvitin, and an amino acid polymer, distributed within said liposomal carrier, said sequestering agent being present in an amount effective to reduce leakage of the diagnostic or therapeutic agent from the liposomal construct prior to delivery and being in addition to said diagnostic or therapeutic agent.

5. A liposomal construct of claim 1 wherein the amino acid polymer comprises a copolymer of aspartic acid and glutamic acid.

6. A liposomal construct of claim 2 wherein the targeting moiety comprises a biliary-attracted molecule.

7. A liposomal construct of claim 6 wherein the biliary-attracted molecule is selected from the group consisting of substituted iminodiacetic acids, N'-substituted derivatives of ethylene diamine-N,N-diacetic acid (EDDA), hepatobiliary dyes, hepatobiliary contrast agents, bile salts, hepatobiliary thiol complexes, and hepatobiliary complexes (including hepatobiliary amine complexes).

8. A liposomal construct of claim 6 wherein the biliary-attracted molecule is selected from the group consisting of N-(2,6-diisopropylphenylcarbamoylmethyl)-iminodiacetic acid, N-(2,6-diethylphenylcarbamoylmethyl)iminodiacetic acid, N-(2,6-dimethylphenylcarbamoylmethyl) iminodiacetic acid, N-(4-isopropylphenylcarbamoylmethyl) iminodiacetic acid, N-(4-butylphenylcarbamoylmethyl) iminodiacetic acid, N-(2,3-dimethylphenylcarbamoylmeyhyl) iminodiacetic acid, N-(3-butylphenylcarbamoylmethyl)iminodiacetic acid, N-(2-butylphenylcarbamoylmethyl)iminodiacetic acid, N-(4-tertiary-butylphenyl carbamoylmethyl)iminodiacetic acid, N-(3-butoxyphenylcarbamoylmethyl) iminodiacetic acid, N-(2-hexyloxyphenylcarbamoylmethyl)iminodiacetic acid, N-(4-hexyloxyphenylcarbamoylmethyl)iminodiacetic acid; azo substituted iminodiacetic acid, iminodicarboxymethyl-2-naphthyl ketone, phthalein complexone, N-(5,pregnene-3-β-ol-2-oylcarbamoylmethyl) iminodiacetic acid, 3a: 7a: 12a: trihydroxy-24-norchol anyl-23-iminodiacetic acid, N-(3-bromo-2,4,6-trimethylphenylcarbamoylmethyl) iminodiacetic acid, benzimidazole methyliminodiacetic acid, N-(3-cyano-4,5-dimethyl-2-pyrryl-carbamoylmethyl)iminodiacetic acid, ethylenediamine-N,N-bis(-2-hydroxy-5-bromo-phenyl) acetate, N'acyl and N'-sulfonyl ethylene diamine-N,N diacetic acid; N'-acetyl EDDA, N'-benzoyl EDDA, N'-(p-toluenesulfonyl) EDDA, N'-(P-t-butylbenzoyl) EDDA, N'-(benzenesulfonyl) EDDA, N'-(p-chlorobenzenesulfonyl) EDDA, N'(p-ethylbenzenesulfonyl) EDDA, N'-(p-n-propylbenzenesulfonyl) EDDA, N'-(naphthalene-2-sulfonyl) EDDA, N'-(2,5-dimethylbenzenesulfonyl) EDDA; N-(2-acetylnaphthyl) iminodiacetic acid; N-(2-naphthyl) methyl)iminodiacetic acid; rose bengal, congo red, bromosulphthalein, bromophenol blue, phenolphthalein, toluidine blue, indocyanine green, iodipamide, ioglycamic acid, bilirubin, cholyglycyliodohistamine, thyroxineglucuronide, penicillamine, β-mercaptoisobutyric acid, dihydroehioctic acid, 6-mercaptopurine, kethoxal-bis (thiosermicarbazone); 1-hydrazinophthalazine (hydralazine)-sulfonyl urea; pyridoxylidene glutamate, pyridoxylidene isoleucine, pyridoxylidene phenylalanine, pyridoxylidene tryptophan, pyridoxylidene 5-methyl tryptophan; 3-hydroxy-4-formyl-pyridene glutamic acid; tetracycline, 7-carboxy-β-hydroxyquinoline, phenolphthalexon, eosin and verograffim.

9. A liposomal construct for delivering a biogenic amine to the hepatocytes of the liver of a mammal comprising:
   a liposomal carrier;
   b) a biogenic amine selected form the group consisting of L-β-3,4-dihydroxyphenylanine, 3-(2-aminoethyl)-5-hydroxyindole, 2-(4-imidazolyl)ethylamine, 4-[1-hydroxy-2-[(methylamino)]ethyl]-1,2-benzenediol, 1-[3,4-dihydroxyphenyl]-2-aminoethanol, γ-amino-n-butyric acid and acetylcholine entrapped within or associated with said liposomal carrier;
   c) a targeting moiety bound to the surface of said liposomal carrier; wherein said targeting moiety comprises a biliary-attracted molecule which binds to a hepatobiliary receptor in the liver; and
   d) a sequestering agent selected from the group consisting of a nucleotide derivative selected from the group consisting of adenosine 5'-triphosphate (ATP), cytidine 5'-triphosphate (CTP), guanosine 5'-triphosphate (GTP), thymidine 5'-triphosphate (TTP), uridine 5'-triphosphate (UTP), adenosine 5'-diphosphate (ADP), cytidine 5'-diphosphate (CDP), guanosine 5'-diphosphate (GDP), thymidine 5'-diphosphate (TDP), uridine 5'-diphosphate (UDP), adenosine 5'-monophosphate (AMP), cytidine 5'-monophosphate (CMP), guanosine 5'-monophosphate (GMP), thymidine 5'-monophosphate (TMP), uridine 5'-monophosphate (UMP), adenosine 5'-tetraphosphate, guanosine 5'-tetraphosphate and thymidine 5'-tetraphosphate, a polyphosphate derivative selected from the group consisting of phytic acid and the hexaphosphate of inositol and phosvitin, and an amino acid polymer distributed within said liposomal carrier, said sequestering agent being present in an amount effective to reduce leakage of the biogenic amine from the liposomal construct prior to delivery to the liver.

10. A liposomal construct of claim 9 wherein the biogenic amine comprises a sympathomimetic amine or an autacoid.

11. A liposomal construct for delivering a biogenic amine to the hepatocytes of the liver of a mammal comprising:
   a) a liposomal carrier;
   b) a biogenic amine selected from the group consisting of serotonin or a serotonergic agonists entrapped within or associated with said liposomal carrier;

c) a targeting moiety bound to the surface of said liposomal carrier; wherein said targeting moiety comprises a biliary-attracted molecule which binds to a hepatobiliary receptor in the liver; and d) a sequesterning agent distributed within said liposomal carrier, said seouestering agent being present in an amount effective to reduce leakage of the biogenic amine from the liposomal construct prior to delivery to the liver.

12. A liposomal construct of claim 9 wherein the amino acid polymer comprises a copolymer of aspartic acid and glutamic acid.

13. A liposomal construct of claim 9 wherein the biliary-attracted molecule is selected from the group consisting of substituted iminodiacetic acids, N'-substituted derivatives of ethylene diamine-N,N-diacetic acid (EDDA), hepatobiliary dyes, hepatobiliary contrast agents, bile salts, hepatobiliary thiol complexes, and hepatobiliary complexes (including hepatobiliary amine complexes).

14. A liposomal construct of claim 9 wherein the biliary-attracted molecule is selected from the group consisting of N-(2,6-diisopropylphenylcarbamoylmethyl)-iminodiacetic acid, N-(2,6-diethylphenyl carbamoylmethyl)iminodiacetic acid, N-(2,6-dimnethylphenylcarbamoylmethyl) iminodiacetic acid, N-(4-isopropylphenylcarbamoylmethyl) iminodiacetic acid, N-(4-butylphenylcarbamoylmethyl) iminodiacetic acid, N-(2,3-dimethylphenylcarbamoyl methyl)iminodiacetic acid, N-(3-butylphenylcarbamoylmethyl)iminodiacetic acid, N-(2-butylphenylcarbamoylmethyl)iminodiacetic acid, N-(4-tertiary-butylphenyl carbamoylmethyl)iminodiacetic acid, N-(3-butoxyphenylcarbamoylmethyl) iminodiacetic acid, N-(2-hexyloxyphenylcarbamoylmethyl)iminodiacetic acid, N-(4-hexyloxyphenylcarbamoylmethyl)iminodiacetic acid; azo substituted iminodiacetic acid, iminodicarboxymethyl-2-naphthyl ketone, phthalein complexone, N-(5,pregnene-3-β-ol-2-oylcarbamoylmethyl)iminodiacetic acid, 3a: 7a: 12a: trihydroxy-24-norchol anyl-23-iminodiacetic acid, N-(3-bromo-2,4,6-trimethylphenylcarbamoylmethyl) iminodiacetic acid, benzimidazole methyliminodiacetic acid, N-(3-cyano-4,5-dimethyl-2-pyrrylcarbamoylmethyl) iminodiacetic acid, ethylenediamine-N,N-bis(-2-hydroxy-5-bromophenyl) acetate, N'acyl and N'-sulfonyl ethylene diamnine-N,N diacetic acid; N'-acetyl EDDA, N'-benzoyl EDDA, N'-(p-toluenesulfonyl) EDDA, N'-(P-t-butylbenzoyl) EDDA, N'-(benzenesulfonyl) EDDA, N'-(p-chlorobenzenesulfonyl) EDDA, N'(p-ethylbenzenesulfonyl) EDDA, N'-(p-n-propylbenzenesulfonyl) EDDA, N'-(naphthalene-2-sulfonyl) EDDA, N'-(2,5-dimethylbenzenesulfonyl) EDDA; N-(2-acetylnaphthyl) iminodiacetic acid; N-(2-naphthyl)methyl)iminodiacetic acid; rose bengal, congo red, bromosulphthalein, bromophenol blue, phenolphthalein, toluidine blue, indocyanine green, iodipamide, ioglycamic acid, bilirubin, cholyglycyliodohistamine, thyroxineglucuronide, penicillamine, β-mercaptoisobutyric acid, dihydroehioctic acid, 6-mercaptopurine, kethoxal-bis(thiosemicarbazone); 1-hydrazinophthalazine(hydralazine)-sulfonyl urea; pyridoxylidene glutamate, pyridoxylidene isoleucine, pyridoxylidene phenylalanine, pyridoxylidene tryptophan, pyridoxylidene 5-methyl tryptophan; 3-hydroxy-4-formyl-pyridene glutamic acid; tetracycline, 7-carboxy-β-hydroxyquinoline, phenolphthalexon, eosin and verograffin.

15. A liposomal construct of claim 9 wherein the liposomal carrier comprises a liposomal membrane.

16. A liposomal construct of claim 9 further comprising a masking agent in intimate association therewith to protect said liposomal carrier from immunoreactive attack.

17. A liposomal construct for delivering serotonin or a serotonergic agonist to the hepatocytes of the liver of a mammal comprising:

a) a liposomal carrier;

b) serotonin or a serotonergic agonist entrapped within or associated with said liposomal carrier;

c) a targeting moiety bound to the surface of said liposomal carrier; wherein said targeting moiety comprises a biliary-attracted molecule which binds to a hepatobiliary receptor in the liver; and d) a sequestering agent selected from the group consisting of a nucleotide derivative selected from the group consisting of adenosine 5'-triphosphate (ATP), cytidine 5'-triphosphate (CTP), guanosine 5'-triphosphate (GTP), thymidine 5'-triphosphate (TTP), uridine 5'-triphosphate (UTP), adenosine 5'-diphosphate (ADP), cytidine 5'-diphosphate (CDP), guanosine 5'-diphosphate (GDP), thymidine 5'-diphosphate (TDP), uridine 5'-diphosphate (UDP), adenosine 5'-monophosphate (AMP), cytidine 5'-monophosphate (CMP), guanosine 5'-monophosphate (GMP), thymidine 5'-monophosphate (TMP), uridine 5'-monophosphate (UMP), adenosine 5'-tetraphosphate, guanosine 5'-tetraphosphate and thymidine 5'-tetraphosphate, a polyphosphate derivative selected from the group consisting of phytic acid and the hexaphosphate of inositol and phosvitin, and an amino acid polymer distributed within said liposomal carrier, said sequestering agent being present in an amount effective to reduce leakage of the serotonin or serotonergic agonist from the liposomal construct prior to delivery to the liver.

18. A liposomal construct of claim 17 wherein the amino acid polymer comprises a copolymer of aspartic acid and glutamic acid.

19. A liposomal construct of claim 17 wherein the biliary-attracted molecule is selected from the group consisting of substituted iminodiacetic acids, N'-substituted derivatives of ethylene diamine-N,N-diacetic acid (EDDA), hepatobiliary dyes, hepatobiliary contrast agents, bile salts, hepatobiliary thiol complexes, and hepatobiliary complexes (including hepatobiliary amine complexes).

20. A liposomal construct of claim 17 wherein the biliary-attracted molecule is selected from the group consisting of N-(2,6-diisopropylphenylcarbamoylmethyl)-iminodiacetic acid, N-(2,6-diethylphenyl carbamoylmethyl)iminodiacetic acid, N-(2,6-dimethylphenylcarbamoylmethyl) iminodiacetic acid, N-(4-isopropylphenylcarbamoylmethyl) iminodiacetic acid, N-(4-butylphenylcarbamoylmethyl) iminodiacetic acid, N-(2,3-dimethylphenylcarbamoyl methyl)iminodiacetic acid, N-(3-butylphenylcarbamoylmethyl)iminodiacetic acid, N-(2-butylphenylcarbamoylmethyl)iminodiacetic acid, N-(4-tertiary-butylphenyl carbamoylmethyl)iminodiacetic acid, N-(3-butoxyphenylcarbamoylmethyl) iminodiacetic acid, N-(2-hexyloxyphenylcarbamoylmethyl)iminodiacetic acid, N-(4-hexyloxyphenylcarbamoylmethyl)iminodiacetic acid; azo substituted imninodiacetic acid, iminodicarboxymethyl-2-naphthyl ketone, phthalein complexone, N-(5, pregnene-3-β-ol-2-oylcarbamoylmethyl)iminodiacetic acid, 3a: 7a: 12a: trihydroxy-24-norchol anyl-23-iminodiacetic acid, N-(3-bromo-2,4,6-trimethylphenylcarbamoylmethyl) iminodiacetic acid, benzimidazole methyliminodiacetic acid, N-(3-cyano-4,5-dimethyl- 2-pyrrylcarbamoylmethyl) iminodiacetic acid, ethylenediamine-N,N-bis(-2-hydroxy-5-bromo-phenyl) acetate, N'acyl and N'-sulfonyl ethylene diamine-N,N diacetic acid; N'-acetyl EDDA, N'-benzoyl EDDA, N'-(p-toluenesulfonyl) EDDA, N'-(P-t-butylbenzoyl) EDDA, N'-(benzenesulfonyl) EDDA, N'-(p-chlorobenzenesulfonyl) EDDA, N'(p-ethylbenzenesulfonyl) EDDA, N'-(p-n-propylbenzenesulfonyl) EDDA, N'-(naphthalene-2-sulfonyl) EDDA, N'-(2,5-dimethylbenzenesulfonyl) EDDA; N-(2-acetylnaphthyl) iminodiacetic acid; N-(2-naphthyl)methyl)iminodiacetic acid; rose bengal, congo red, bromosulphthalein, bromophenol blue, phenolphthalein, toluidine blue, indocyanine green, iodipamide, ioglycamic acid, bilirubin, cholyglycyliodohistamine, thyroxineglucuronide, penicillamine, β-mercaptoisobutyric acid, dihydroehioctic acid, 6-mercaptopurine, kethoxal-bis(thiosemicarbazone); 1-hydrazinophthalazine(hydralazine)-sulfonyl urea; pyridoxylidene glutamate, pyridoxylidene isoleucine, pyridoxylidene phenylalanine, pyridoxylidene tryptophan, pyridoxylidene 5-methyl tryptophan; 3-hydroxy-4-formyl-pyridene glutamic acid; tetracycline, 7-carboxy-β-hydroxyquinoline, phenolphthalexon, eosin and verograffm.

21. A liposomal construct of claim 17 wherein the liposomal carrier comprises a liposomal membrane.

22. A liposomal construct of claim 17 further comprising a masking agent in intimate association therewith to protect said liposomal carrier from immunoreactive attack.

23. A liposomal construct for delivering serotonin or a serotonergic agonist to the liver of a mammal comprising:
   a) a liposomal carrier;
   b) serotonin or a serotonergic agonist entrapped within or associated with said liposomal carrier;
   c) a targeting moiety bound to the surface of said liposomal carrier; wherein said targeting moiety comprises a biliary-attracted molecule which binds to a hepatobiliary receptor in the liver; and
   d) a sequestering agent distributed within said liposomal carrier, said sequestering agent being present in an amount effective to reduce leakage of the serotonin or serotonergic agonist from the liposomal construct prior to delivery to the liver, said sequestering agent comprising a nucleotide derivative selected from the group consisting of adenosine 5'-triphosphate, cytidine 5'-triphosphate, guanosine 5'-triphosphate, thymidine 5'-triphosphate, uridine 5'-triphosphate, adenosine 5'-diphosphate, cytidine 5'-diphosphate, guanosine 5'-diphosphate, thymidine 5'-diphosphate, uridine 5'-diphosphate, adenosine 5'-monophosphate, cytidine 5'-monophosphate, guanosine 5'-monophosphate, thymidine 5'-monophosphate, uridine 5'-monophosphate, adenosine 5'-tetraphosphate, guanosine 5'-tetraphosphate and thymidine 5'-tetraphosphate.

24. A liposomal construct of claim 23 wherein the biliary-attracted molecule is selected from the group consisting of substituted iminodiacetic acids, N'-substituted derivatives of ethylene diamine-N,N-diacetic acid (EDDA), hepatobiliary dyes, hepatobiliary contrast agents, bile salts, hepatobiliary thiol complexes, and hepatobiliary complexes (including hepatobiliary amine complexes).

25. A liposomal construct of claim 23 further comprising a masking agent in intimate association therewith to protect said liposomal construct from immunoreactive attack.

26. A pharmaceutical composition comprising a liposomal construct of claim 1 and a pharmaceutically acceptable excipient.

27. A pharmaceutical composition comprising a liposomal construct of claim 9 and a pharmaceutically acceptable excipient.

28. A pharmaceutical composition comprising a liposomal construct of claim 17 and a pharmaceutically acceptable excipient.

29. A pharmaceutical composition comprising a liposomal construct of claim 23 and a pharmaceutically acceptable excipient.

30. A pharmaceutical composition for inducing a serotonergic response in the liver of a mammal comprising:
   a) a liposomal carrier;
   b) serotonin or a serotonergic agonist entrapped within or associated with said liposomal carrier;
   c) a targeting moiety bound to the surface of said liposomal carrier; wherein said targeting moiety comprises a biliary-attracted molecule which binds to a hepatobiliary receptor in the liver;
   d) a sequestering agent selected from the group consisting of a nucleotide derivative, selected from the group consisting of adenosine 5'-triphosphate (ATP), cytidine 5'-triphosphate (CTP), guanosine 5'-triphosphate (GTP), thymidine 5'-triphosphate (TTP), uridine 5'-triphosphate (UTP), adenosine 5'-diphosphate (ADP), cytidine 5'-diphosphate (CDP), guanosine 5'-diphosphate (GDP), thymidine 5'-diphosphate (TDP), uridine 5'-diphosphate (UDP), adenosine 5'-monophosphate (AMP), cytidine 5'-monophosphate (CMP), guanosine 5'-monophosphate (GMP), thymidine 5'-monophosphate (TMP), uridine 5'-monophosphate (UMP), adenosine 5'-tetraphosphate, guanosine 5'-tetraphosphate and thymidine 5'-tetraphosphate, a polyphosphate derivative selected from the group consisting of phytic acid and the hexaphosphate of inositol and phosvitin, and an amino acid polymer, distributed within said liposomal carrier, said sequestering agent being present in an amount effective to reduce leakage of the serotonergic agonist from the liposomal construct prior to delivery to the liver;
   e) a masking agent in intimate association therewith to protect said liposomal carrier from immunoreactive attack; and
   a pharmaceutically acceptable excipient.

31. A method of treating a disease state in a mammal responsive to therapy with biogenic arnines which method comprises administering a therapeutically effective amount of a composition of claim 9 to the mammal.

32. A method of treating Type II diabetes in a mammal which method comprises administering a therapeutically effective amount of a pharmaceufical composition of claim 28 to the mammal.

33. A method of treating Type II diabetes in a mammal which method comprises administering a therapeutically effective amount of a pharmaceutical composition of claim 29 to the mammal.

34. A method of treating Type II diabetes in a mammal which method comprises administering a therapeutically effective amount of a pharmaceutical composition of claim 30 to the mammal.

35. A method of treating Type II diabetes in a mammal which method comprises administering a therapeutically effective amount of a pharmacaeutical composition comprising:
   a) a liposomal carrier;
   b) serotonin or a serotonergic agonist entrapped within or associated with said liposomal carrier;
   c) a targeting moiety bound to the surface of said liposomal carrier; wherein said targeting moiety comprises a biliary-attracted molecule which binds to a hepatobiliary receptor in the liver;
   d) a sequestering agent selected from the group consisting of a nucleotide derivative selected from the group consisting of adenosine 5'-triphosphate (ATP), cytidine 5'-triphosphate (CTP), guanosine 5'-triphosphate (GTP), thymidine 5'-triphosphate (TTP), uridine 5'-triphosphate (UTP), adenosine 5'-diphosphate (ADP), cytidine 5'-diphosphate (CDP), guanosine 5'-diphosphate (GDP), thymidine 5'-diphosphate (TDP), uridine 5'-diphosphate (UDP), adenosine 5'-monophosphate (AMP), cytidine 5'-monophosphate (CMP), guanosine 5'-monophosphate (GMP), thymidine 5'-monophosphate (TMP), uridine 5'-monophosphate (UMP), adenosine 5'-tetraphosphate, guanosine 5'-tetraphosphate and thymidine 5'-tetraphosphate, a polyphosphate derivative selected from the group consisting of phytic acid and the hexaphosphate of inositol and phosvitin, and an amino acid polymer distributed within said liposomal carrier, said sequestering agent being present in an amount effective to reduce leakage of the serotonin or serotonergic agonist from the liposomal construct prior to delivery to the liver;

e) a masking agent in intimate association therewith to protect said liposomal carrier from immunoreactive attack; and a pharmaceutically acceptable excipient.

36. A method of claim 35 in which the amount of serotonin is from about 100 to about 200 µg.

* * * * *